US012692470B2

(12) United States Patent　　(10) Patent No.:　US 12,692,470 B2

Guo et al.　　(45) Date of Patent:　　Jul. 28, 2026

(54) METHOD AND DEVICE FOR AUTOMATIC CELL CENTRIFUGAL CLEANING AND MEDIUM REPLACEMENT

(71) Applicant: SHENZHEN CELLBRI BIO-INNOVATION TECHNOLOGY CO., LTD., Shenzhen (CN)

(72) Inventors: Xiaoliang Guo, Shenzhen (CN); Jialin Yao, Shenzhen (CN); Yuanfang Shang, Shenzhen (CN)

(73) Assignee: SHENZHEN CELLBRI BIO-INNOVATION TECHNOLOGY CO., LTD., Shenzhen (CN)

( * ) Notice: Subject to any disclaimer, the term of this patent is extended or adjusted under 35 U.S.C. 154(b) by 696 days.

(21) Appl. No.: 18/028,217

(22) PCT Filed: Sep. 15, 2021

(86) PCT No.: PCT/CN2021/118377

§ 371 (c)(1),
(2) Date: Mar. 24, 2023

(87) PCT Pub. No.: WO2022/062977

PCT Pub. Date: Mar. 31, 2022

(65) Prior Publication Data

US 2023/0374441 A1　　Nov. 23, 2023

(30) Foreign Application Priority Data

Sep. 25, 2020　(CN) .......................... 202011024135.3

(51) Int. Cl.
C12M 1/36　　(2006.01)
B04B 13/00　　(2006.01)
(Continued)

(52) U.S. Cl.
CPC ............. *C12M 47/04* (2013.01); *B04B 13/00* (2013.01); *C12M 41/44* (2013.01); *C12M 41/48* (2013.01)

(58) Field of Classification Search
CPC ......... B04B 11/04; B04B 1/06; B04B 5/0442; B04B 11/082; B04B 15/08; B04B 11/02;
(Continued)

(56) References Cited

U.S. PATENT DOCUMENTS 3,561,672 A　　2/1971　Schlutz et al.
5,141,486 A *　8/1992　Antwiler ............. A61M 1/3696
494/35

(Continued)

FOREIGN PATENT DOCUMENTS

CN　　204276166 U　　4/2015
CN　　109022340 A　　12/2018
(Continued)

*Primary Examiner* — Charles Cooley

(74) *Attorney, Agent, or Firm* — Bayramoglu Law Offices LLC

(57)　　　　　ABSTRACT

A method for automatic cell centrifugal cleaning and medium replacement includes: obtaining a cell volume and a critical value of a centrifugal device after centrifugal stabilization of the centrifugal device; and performing, according to a magnitude relationship between the cell volume and the critical value of the centrifugal device, a velocity reduction process on a centrifugal chamber by combining the cell volume and the centrifugal chamber information. The extracted volume is changed by velocity-reduced rotation, and the rotation at a reduced velocity is adjusted according to the magnitude relationship between the cell volume and the critical value of the centrifugal device. The optimal cleaning and medium replacement effect on cells of different volumes can be realized. A high capture rate and a high medium replacement rate are
(Continued)

Obtaining a cell volume and a critical value of a centrifugal device after a centrifugal stabilization of the centrifugal device;　　　　　S1

Performing, according to a magnitude relationship between the cell volume and the critical value of the centrifugal device, a velocity reduction process on a centrifugal chamber by combining the cell volume and centrifugal chamber information.　　　　　S2 obtained and maximized from different volumes of cell samples in the fixed parameters of the centrifugal chamber.

13 Claims, 4 Drawing Sheets

(51) Int. Cl.
*C12M 1/00* (2006.01)
*C12M 1/34* (2006.01)

(58) Field of Classification Search
CPC ... B04B 7/08; B04B 2005/0464; B04B 13/00; C12M 25/06; C12M 33/10; C12M 47/02; C12M 23/28; C12M 47/04; C12M 41/44; C12M 41/48; C12M 41/00; C12M 47/10; B01D 21/262; C12N 1/02
USPC ......... 494/12, 83, 41, 38, 43, 84–85, 56, 36, 494/25–26
See application file for complete search history.

(56) References Cited

U.S. PATENT DOCUMENTS

| | | | | |
|---|---|---|---|---|
| 5,733,253 A * | 3/1998 | Headley | ............. | A61M 1/3693 494/23 |
| 5,876,611 A * | 3/1999 | Shettigar | ............. | A61M 1/3692 210/650 |
| 5,885,239 A * | 3/1999 | Headley | ............... | B04B 5/0442 494/9 |
| 5,976,388 A * | 11/1999 | Carson | ............... | A61M 1/3696 494/67 |
| 6,241,649 B1 * | 6/2001 | Zanella | ................. | B04B 5/0442 494/10 |
| 6,352,499 B1 * | 3/2002 | Geigle | ................. | B04B 5/0442 494/37 |
| 6,416,456 B2 * | 7/2002 | Zanella | ................... | B04B 11/04 494/37 |
| 6,716,151 B2 * | 4/2004 | Panzani | .............. | A61M 1/3696 494/10 |
| 7,001,323 B2 * | 2/2006 | Panzani | .............. | A61M 1/0281 494/37 |
| 7,156,800 B2 * | 1/2007 | Panzani | ................. | B04B 13/00 494/10 |
| 7,452,322 B2 * | 11/2008 | Headley | ............... | B04B 5/0428 494/45 |
| 10,683,478 B1 * | 6/2020 | Ma | ......................... | C12M 23/14 |
| 2002/0158029 A1 * | 10/2002 | Panzani | .............. | A61M 1/3696 210/782 |
| 2004/0030516 A1 | 2/2004 | Dunhill et al. | | |
| 2004/0104182 A1 | 6/2004 | Holmes et al. | | |
| 2014/0045670 A1 | 2/2014 | Smith et al. | | |
| 2017/0029762 A1 * | 2/2017 | Turgut | ................. | C12N 5/0647 |
| 2020/0355585 A1 * | 11/2020 | Ishige | ..................... | B01L 3/502 |
| 2023/0374441 A1 * | 11/2023 | Guo | ....................... | C12M 47/04 |

FOREIGN PATENT DOCUMENTS

| | | | | | |
|---|---|---|---|---|---|
| CN | 110621410 A | 12/2019 | | | |
| CN | 112175827 A | 1/2021 | | | |
| EP | 0420153 A1 | 4/1991 | | | |
| EP | 0868215 A1 | 10/1998 | | | |
| EP | 2664383 A1 | 11/2013 | | | |
| KR | 20180103692 A | 9/2018 | | | |
| WO | WO-2022062977 A1 * | 3/2022 | ........... | C12M 47/04 |

* cited by examiner

METHOD AND DEVICE FOR AUTOMATIC CELL CENTRIFUGAL CLEANING AND MEDIUM REPLACEMENT

CROSS REFERENCE TO THE RELATED APPLICATIONS

This application is the national phase entry of International Application No. PCT/CN2021/118377, filed on Sep. 15, 2021, which is based upon and claims priority to Chinese Patent Application No. 202011024135.3, filed on Sep. 25, 2020, the entire contents of which are incorporated herein by reference.

TECHNICAL FIELD

The present invention relates to the technical field of cell culture, and more particularly, to a method and a device for automatic cell centrifugal cleaning and medium replacement.

BACKGROUND

Cell culture is the most basic part of the research field of cell biology and life science. Cell culture is implemented by multiplying the cells in an artificial environment using nutrients and is used for various objectives. In the process of cell culture, a centrifugal separation device can effectively realize solid-liquid separation of cell cultures and is used for the operations of cleaning and medium replacement in cell culture. These operations are frequently needed in cell experiments, but manual centrifugation and medium replacement operation often have poor efficiency, and also, frequent manual operations are highly likely to introduce some impurities to the culture medium, causing contamination to the culture medium and spoiling the cell culture environment. Therefore, the automatic cell centrifugation device has a great development prospect.

In the existing automatic cell centrifugation devices, cells are centrifuged to the axial outer wall of a centrifugal container under the action of centrifugal force. To realize automatic liquid extraction, it is necessary to arrange an automatic liquid outlet in the appropriate axial position. In this case, the velocity of the centrifugation device has an important influence on the effect of centrifugation.

Therefore, how to control the automatic cell centrifugal device to better realize the automatic liquid extraction has become an urgent problem to be solved in the art.

SUMMARY

Embodiments of the present invention provide a method and a device for automatic cell centrifugal cleaning and medium replacement, which solve the technical problems proposed in the background technology, or at least partially solve the technical problems proposed in the background technology.

In the first aspect, an embodiment of the present invention provides a method for automatic cell centrifugal cleaning and medium replacement, including:

obtaining a cell volume and a critical value of a centrifugal device after centrifugal stabilization of the centrifugal device; and performing, according to a magnitude relationship between the cell volume and the critical value of the centrifugal device, a velocity reduction process on a centrifugal chamber by combining the cell volume and centrifugal chamber information.

More specifically, the centrifugal chamber information includes chamber length information, chamber height information, and chamber radius information.

The chamber length information is the distance from the outer wall of the centrifugal chamber to an outlet position of the centrifugal device.

The chamber height information is the height of the centrifugal chamber.

The chamber radius information is the radius of the centrifugal chamber.

More specifically, the step of performing, according to the magnitude relationship between the cell volume and the critical value of the centrifugal device, the velocity reduction process on the centrifugal chamber by combining the cell volume and the centrifugal chamber information specifically includes:

when the cell volume is less than the critical value of the centrifugal device, calculating a rotation velocity for a velocity reduction of the centrifugal chamber according to the cell volume, the chamber length information, and the chamber radius information, such that the velocity reduction process is performed on the centrifugal chamber according to the rotation velocity for the velocity reduction of the centrifugal chamber.

More specifically, the step of performing, according to the magnitude relationship between the cell volume and the critical value of the centrifugal device, the velocity reduction process on the centrifugal chamber by combining the cell volume and the centrifugal chamber information specifically further includes:

when the cell volume is equal to the critical value of the centrifugal device, calculating a rotation velocity for a velocity reduction of the centrifugal chamber according to the chamber length information and the chamber radius information, such that the velocity reduction process is performed on the centrifugal chamber according to the rotation velocity for the velocity reduction of the centrifugal chamber.

More specifically, the step of performing, according to the magnitude relationship between the cell volume and the critical value of the centrifugal device, the velocity reduction process on the centrifugal chamber by combining the cell volume and the centrifugal chamber information specifically further includes:

when the cell volume is larger than the critical value of the centrifugal device, calculating a rotation velocity for a velocity reduction of the centrifugal chamber according to the cell volume, the chamber length information, the chamber radius information, and the height of the centrifugal chamber, such that the velocity reduction process is performed on the centrifugal chamber according to the rotation velocity for the velocity reduction of the centrifugal chamber.

In the second aspect, an embodiment of the present invention provides a device for automatic cell centrifugal cleaning and medium replacement, including:

an acquisition module configured to obtain a cell volume and a critical value of a centrifugal device after centrifugal stabilization of the centrifugal device; and a velocity reduction and medium replacement module configured to perform, according to a magnitude relationship between the cell volume and the critical value of the centrifugal device, a velocity reduction process on a centrifugal chamber by combining the cell volume and centrifugal chamber information.

More specifically, the centrifugal chamber information includes chamber length information, chamber height information, and chamber radius information.

The chamber length information is the distance from the outer wall of the centrifugal chamber to an outlet position of the centrifugal device.

The chamber height information is the height of the centrifugal chamber.

The chamber radius information is the radius of the centrifugal chamber.

In the third aspect, an embodiment of the present invention provides an electronic device, including a memory, a processor, and a computer program that is stored on the memory and configured to run on the processor. When the computer program is executed by the processor, steps of the method for automatic cell centrifugal cleaning and medium replacement according to the first aspect are implemented.

In the fourth aspect, an embodiment of the present invention provides a non-transient computer-readable storage medium, storing a computer program. When the computer program is executed by a processor, steps of the method for automatic cell centrifugal cleaning and medium replacement according to the first aspect are implemented.

In the method and device for automatic cell centrifugal cleaning and medium replacement according to the embodiments of the present invention, the extracted volume is changed by velocity-reduced rotation, and the rotation at a reduced velocity is adjusted according to the magnitude relationship between the cell volume and the critical value of the centrifugal device. In this way, the optimal cleaning and medium replacement effect on cells of different volumes can be realized, thereby realizing the automatic cell centrifugal cleaning and medium replacement.

BRIEF DESCRIPTION OF THE DRAWINGS

To more clearly illustrate the technical solutions in the embodiments of the present invention or the prior art, the drawings that need to be used in the description of the embodiments or the prior art are briefly introduced below. The drawings described below are some embodiments of the present invention. For those skilled in the art, other drawings may be obtained according to these drawings without creative work.

FIG. 7 is a diagram showing the relationship between the residual liquid volume and the rotation velocity by reducing the centrifugal rotation velocity according to another embodiment of the present invention.

DETAILED DESCRIPTION OF THE EMBODIMENTS

To make the objective, technical solution, and advantages of the embodiments of the present invention more clear, the technical solutions in the embodiments of the present invention will be described clearly and completely in conjunction with the drawings in the embodiments of the present invention. The described embodiments are some embodiments of the present invention, rather than all embodiments. Based on the embodiments of the present invention, all other embodiments obtained by those having ordinary skill in the art without creative work shall fall within the scope of protection of the present invention.

Figure 1:
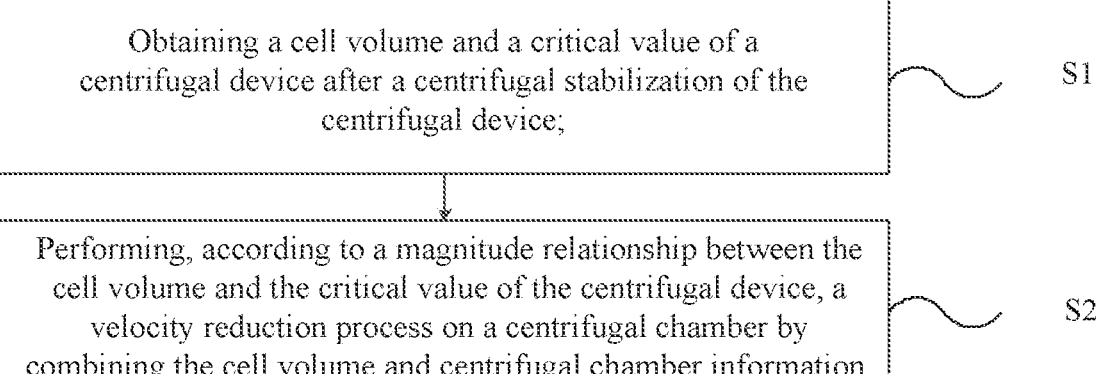
FIG. 1 is a schematic diagram showing a flow chart of a method for automatic cell centrifugal cleaning and medium replacement according to an embodiment of the present invention.

FIG. 1 is a schematic diagram showing a flow chart of a method for automatic cell centrifugal cleaning and medium replacement according to an embodiment of the present invention. As shown in FIG. 1, the method includes:

Step S1: a cell volume and a critical value of a centrifugal device are obtained after centrifugal stabilization of the centrifugal device.

Specifically, before the centrifugal stabilization of the centrifugal device, the centrifugal device performs centrifugation by an acceleration of more than 200 g for more than 1 min, so that cells or other organisms are centrifuged to the axial outer wall of a centrifugal chamber. After the centrifugal stabilization, the solution is extracted from the outlet as much as possible, until the surface of the solution reaches the outlet, and then the rotation velocity is slowly reduced.

In the embodiment of the present invention, the critical value of the centrifugal device is $V_{cell\ critical}=\pi HLR$.

In the embodiment of the present invention, the cell volume can be measured and obtained in advance before centrifugation and can also be calculated concretely. The calculation method of the cell volume is as follows:

When the cell volume is less than the critical value $V_{cell\ critical}=\pi HLR$ and the height of the cells in the centrifugal chamber is S, $$V_{cell}=\pi SLR.$$

When the cell volume is larger than the critical value $V_{cell\ critical}=\pi HLR$, the height of the cells in the centrifugal chamber is S, and the cells form a trapezoidal accumulation surface after centrifugation, and the cell volume is calculated as follows:

$$V_{cell}=\pi HR(T+L),$$

where $V_{cell}$ denotes the cell volume, L denotes the chamber length information, R denotes the chamber radius information, S denotes the height of the cells in the centrifugal chamber, and the height of the centrifugal chamber is H.

Step S2: according to a magnitude relationship between the cell volume and the critical value of the centrifugal device, a velocity reduction process is performed on the centrifugal chamber by combining the cell volume and the centrifugal chamber information.

Specifically, the magnitude relationship between the cell volume and the critical value of the centrifugal device is divided into three cases: 1) the cell volume is larger than the critical value of the centrifugal device, 2) the cell volume is less than the critical value of the centrifugal device, and 3) the cell volume is equal to the critical value of the centrifugal device. Different rotation velocity calculation methods for the velocity reduction of the centrifugal chamber are determined to obtain the velocity reduction information of the centrifugal chamber and then the velocity reduction process is performed on the centrifugal chamber.

In the embodiment of the present invention, the velocity reduction process is performed on the centrifugal chamber to ensure that a high capture rate and a high medium replacement rate are obtained and maximized from cell samples of different volumes in the fixed parameters of the centrifugal chamber.

In the embodiment of the present invention, the extracted volume is changed by velocity-reduced rotation, and the rotation at a reduced velocity is adjusted according to the magnitude relationship between the cell volume and the critical value of the centrifugal device. In this way, the optimal cleaning and medium replacement effect on cells of different volumes can be realized, thereby realizing the automatic cell centrifugal cleaning and medium replacement.

Based on the above embodiment, the centrifugal chamber information includes chamber length information, chamber height information, and chamber radius information.

The chamber length information L is the distance from the outer wall of the centrifugal chamber to the outlet position of the centrifugal device.

The chamber height information H is the height of the centrifugal chamber.

The chamber radius information R is the radius of the centrifugal chamber.

More specifically, the step of performing, according to the magnitude relationship between the cell volume and the critical value of the centrifugal device, the velocity reduction process on the centrifugal chamber by combining the cell volume and the centrifugal chamber information specifically includes:

When the cell volume is less than the critical value of the centrifugal device, a rotation velocity for a velocity reduction of the centrifugal chamber is calculated according to the cell volume, the chamber length information, and the chamber radius information, such that the velocity reduction process is performed on the centrifugal chamber according to the rotation velocity for the velocity reduction of the centrifugal chamber.

Figure 2:
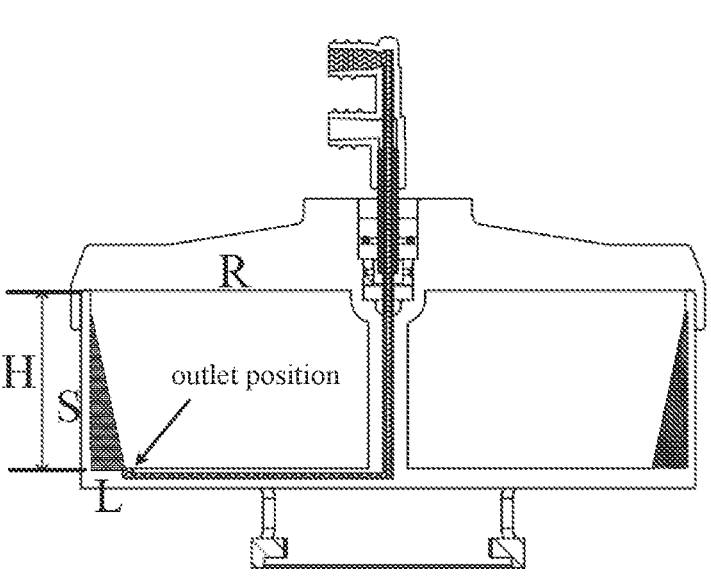
FIG. 2 is a schematic diagram showing a centrifugal device in which a cell volume is less than a critical value according to an embodiment of the present invention.

According to the cell volume, the chamber length information, and the chamber radius information, the rotation velocity for the velocity reduction of the centrifugal chamber is specifically calculated as follows. FIG. 2 is a schematic diagram showing the centrifugal device in which the cell volume is less than the critical value according to an embodiment of the present invention. As shown in FIG. 2, the distance from the outer part of the chamber's outer wall to the outlet position is L, the radius of the centrifugal chamber is R, and the height of the centrifugal chamber is H. When the cell volume is less than the critical value $V_{cell\ critical}=\pi HLR$, the height of the cells in the centrifugal chamber is S. When the velocity of the centrifugal chamber reduces, the rotation velocity is recommended to be $\omega$.

$$V_{cell} = \pi SLR,$$

$$\frac{S}{L} = \frac{\omega^2 R}{g},$$

6

-continued $$\omega = \sqrt{\frac{V_{cell}}{\pi L^2 R^2}g}\,.$$

Based on the above embodiments, the step of performing, according to the magnitude relationship between the cell volume and the critical value of the centrifugal device, the velocity reduction process on the centrifugal chamber by combining the cell volume and the centrifugal chamber information specifically further includes:

When the cell volume is equal to the critical value of the centrifugal device, a rotation velocity for a velocity reduction of the centrifugal chamber is calculated according to the chamber length information and the chamber radius information, such that the velocity reduction process is performed on the centrifugal chamber according to the rotation velocity for the velocity reduction of the centrifugal chamber.

Figure 3:
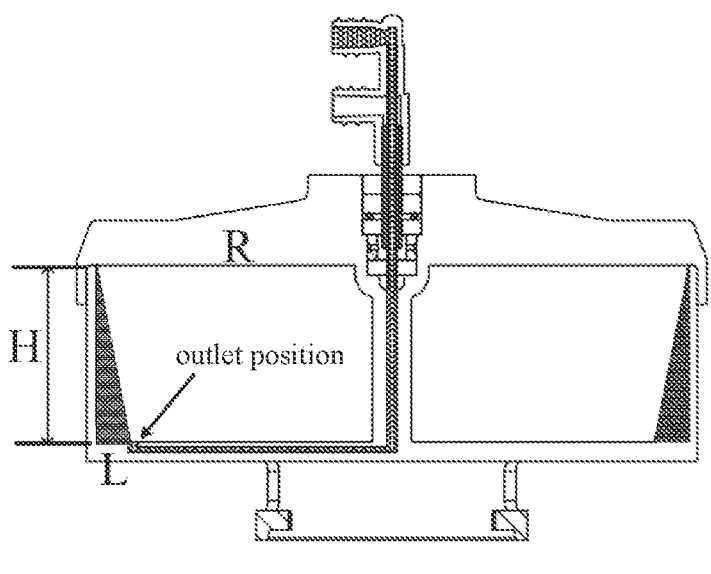
FIG. 3 is a schematic diagram showing the centrifugal device in which the cell volume is equal to the critical value according to an embodiment of the present invention.

According to the chamber length information and the chamber radius information, the rotation velocity for the velocity reduction of the centrifugal chamber is specifically calculated as follows. FIG. 3 is a schematic diagram showing the centrifugal device in which the cell volume is equal to the critical value according to an embodiment of the present invention. As shown in FIG. 3, the distance from the outer part of the chamber's outer wall to the outlet position is L, the radius of the centrifugal chamber is R, and the height of the centrifugal chamber is H. When the cell volume is equal to the critical value $V_{cell\ critical}=\pi HLR$, the height of the cells in the centrifugal chamber is the height H of the centrifugal chamber. When the velocity of the centrifugal chamber reduces, the rotation velocity is recommended to be $\omega$.

$$\frac{H}{L} = \frac{\omega^2 R}{g},$$

$$\omega = \sqrt{\frac{Hg}{LR}}\,,$$

where $V_{cell}$ denotes the cell volume, L denotes the chamber length information, R denotes the chamber radius information, and $\omega$ denotes the rotation velocity for the velocity reduction of the centrifugal chamber.

Based on the above embodiments, more specifically, the step of performing, according to the magnitude relationship between the cell volume and the critical value of the centrifugal device, the velocity reduction process on the centrifugal chamber by combining the cell volume and the centrifugal chamber information specifically further includes:

When the cell volume is larger than the critical value of the centrifugal device, a rotation velocity for a velocity reduction of the centrifugal chamber is calculated according to the cell volume, the chamber length information, the chamber radius information, and the height of the centrifugal chamber, such that the velocity reduction process is performed on the centrifugal chamber according to the rotation velocity for the velocity reduction of the centrifugal chamber.

Figure 4:
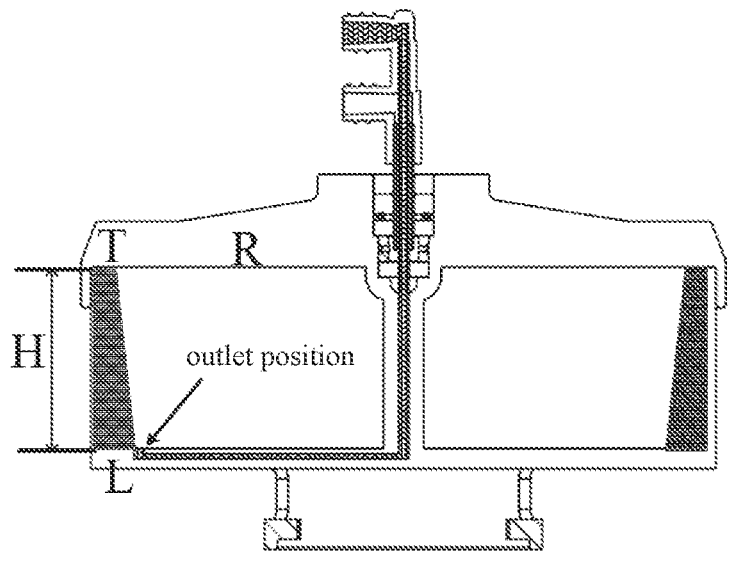
FIG. 4 is a schematic diagram showing the centrifugal device in which the cell volume is larger than the critical value according to an embodiment of the present invention.

According to the cell volume, the chamber length information, the chamber radius information, and the height of the centrifugal chamber, the rotation velocity for the velocity reduction of the centrifugal chamber is specifically calculated as follows. FIG. 4 is a schematic diagram showing the centrifugal device in which the cell volume is larger than the critical value according to an embodiment of the present invention. As shown in FIG. 4, in the embodiment of the present embodiment, the distance from the outer part of the chamber's outer wall to the outlet position is L, the radius of the centrifugal chamber is R, and the height of the centrifugal chamber is H. When the cell volume is larger than the critical value $V_{cell\ critical} = \pi HLR$, the height of the cells in the centrifugal chamber is S, the cells form a trapezoidal accumulation surface after centrifugation, and the length of the upper base of the trapezoid is T. When the velocity of the centrifugal chamber reduces, the rotation velocity is recommended to be $\omega$.

$$V_{cell} = \pi HR(T + L),$$

$$\frac{H}{L-T} = \frac{\omega^2(R-T)}{g},$$

$$\omega = \sqrt{\frac{\pi H^3 R^2 g}{(2\pi LHR - V_{cell})[\pi(R+L)HR - V_{cell}]}}.$$

In the embodiment of the present invention, the extracted volume is changed by velocity-reduced rotation, and the rotation at a reduced velocity is adjusted according to the magnitude relationship between the cell volume and the critical value of the centrifugal device. In this way, the optimal cleaning and medium replacement effect on cells of different volumes can be realized, thereby realizing the automatic cell centrifugal cleaning and medium replacement.

Figure 5:
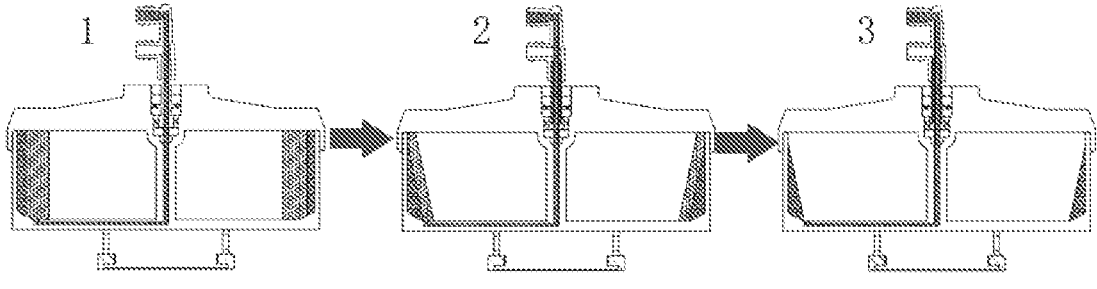
FIG. 5 is a working diagram showing automatic cell centrifugal cleaning and medium replacement according to an embodiment of the present invention.
Figure 6:
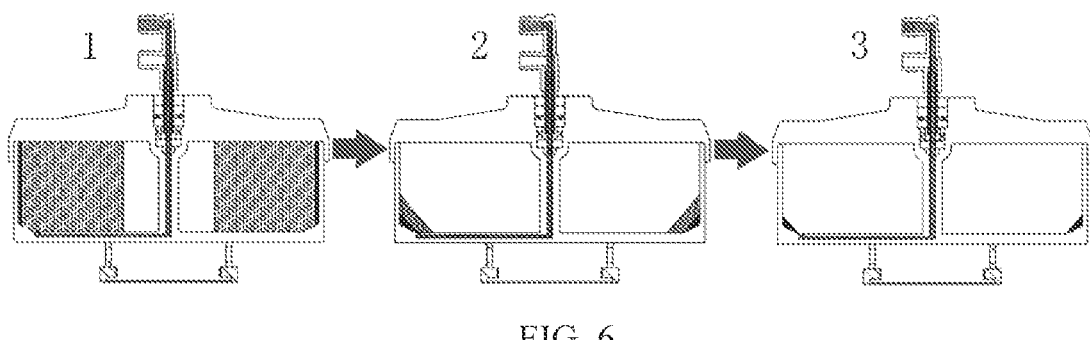
FIG. 6 is a working diagram showing automatic cell centrifugal cleaning and medium replacement according to another embodiment of the present invention.

In another embodiment of the present invention, FIG. 5 is a working diagram of automatic cell centrifugal cleaning and medium replacement according to an embodiment of the present invention, and FIG. 6 is a working diagram of automatic cell centrifugal cleaning and medium replacement according to another embodiment of the present invention. As shown in FIGS. 5 and 6, step 1: the centrifugal device performs centrifugation by an acceleration of more than 200 g for more than 1 min, and cells or other organisms are centrifuged to the axial outer wall of a centrifugal chamber. An outlet is arranged at a certain distance from the outer part of the chamber's outer wall, and the distance can be set to a distance corresponding to the maximum volume of processing the cell samples. Step 2: After the centrifugal stabilization, the solution is extracted from the outlet as much as possible, until the surface of the solution reaches the outlet, and then the rotation velocity is slowly reduced. As the velocity reduces, the surface of the solution will be changed. Step 3: Finally, all the unwanted solution is extracted from the outlet, the cells are left after centrifugation.

FIG. 7 is a diagram showing the relationship between the residual liquid volume and the rotation velocity by reducing the centrifugal rotation velocity according to another embodiment of the present invention. As shown in FIG. 7, for cell centrifugation, the cell medium replacement of 95% is realized, the capture rate of the cells is more than 95%, and the cell activity remains basically unchanged.

Figure 8:
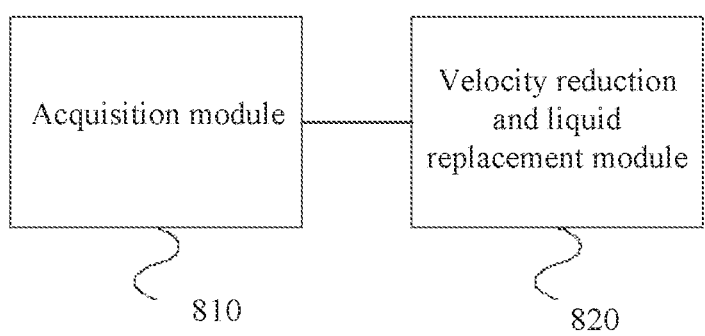
FIG. 8 is a schematic diagram showing a device for automatic cell centrifugal cleaning and medium replacement according to an embodiment of the present invention.

FIG. 8 is a schematic diagram of a device for automatic cell centrifugal cleaning and medium replacement according to an embodiment of the present invention. As shown in FIG. 8, the device includes an acquisition module 810 and a velocity reduction and medium replacement module 820. Specifically, the acquisition module 810 is configured to obtain a cell volume and a critical value of a centrifugal device after centrifugal stabilization of the centrifugal device. Specifically, the velocity reduction and medium replacement module 820 is configured to perform, according to a magnitude relationship between the cell volume and the critical value of the centrifugal device, a velocity reduction process on a centrifugal chamber by combining the cell volume and the centrifugal chamber information.

More specifically, the centrifugal chamber information includes chamber length information, chamber height information, and chamber radius information.

The chamber length information is the distance from the outer wall of the centrifugal chamber to the outlet position of the centrifugal device.

The chamber height information is the height of the centrifugal chamber.

The chamber radius information is the radius of the centrifugal chamber.

The device provided by the embodiment of the present invention is configured for executing the above method embodiments, and the specific flow and details are referred to the above embodiments, which will not be repeated here.

In the embodiment of the present invention, the extracted volume is changed by velocity-reduced rotation, and the rotation at a reduced velocity is adjusted according to the magnitude relationship between the cell volume and the critical value of the centrifugal device. In this way, the optimal cleaning and medium replacement effect on cells of different volumes can be realized, thereby realizing the automatic cell centrifugal cleaning and medium replacement.

Figure 9:
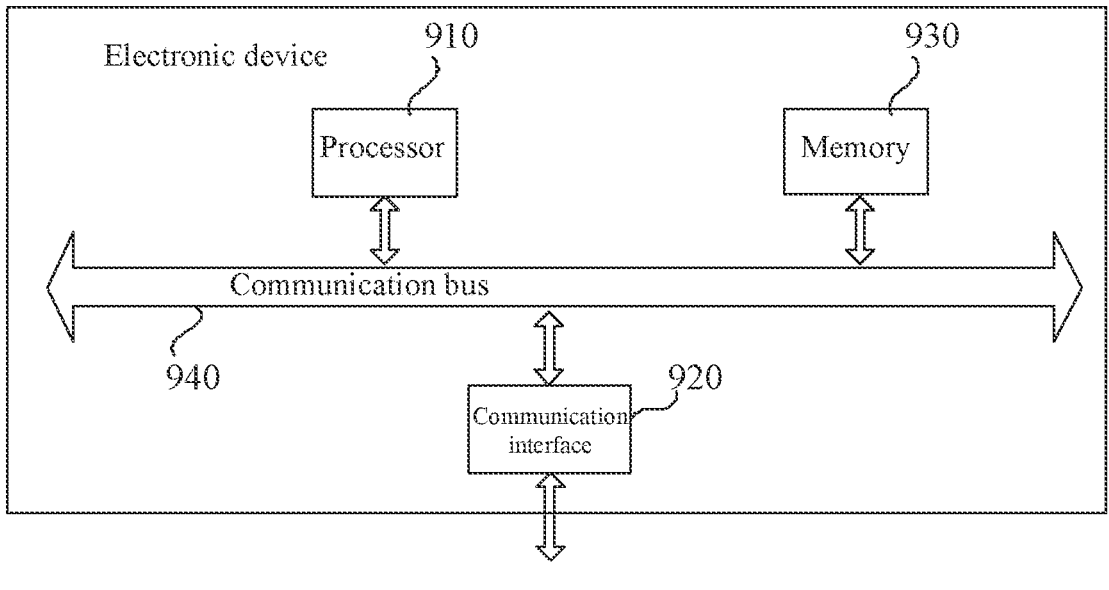
FIG. 9 is a schematic diagram showing the structure of an electronic device according to an embodiment of the present invention.

FIG. 9 is a schematic diagram of the structure of an electronic device according to an embodiment of the present invention. As shown in FIG. 9, the electronic device may include the processor 910, the communication interface 920, the memory 930, and the communication bus 940. Specifically, the processor 910, the communication interface 920, and the memory 930 communicate with each other through the communication bus 940. The processor 910 can invoke logic instructions in the memory 930 to execute the following method: obtaining a cell volume and a critical value of a centrifugal device after centrifugal stabilization of the centrifugal device; and performing, according to a magnitude relationship between the cell volume and the critical value of the centrifugal device, a velocity reduction process on a centrifugal chamber by combining the cell volume and the centrifugal chamber information.

In addition, the logic instructions in the above memory 930 can be implemented in the form of a software function unit and can be stored in a computer-readable storage medium when sold or used as an independent product. Based on this understanding, the technical solution of the present invention, in essence, is that the part that contributes to the prior art or a part of the technical solution can be reflected in the form of a software product. The computer software product is stored in a storage medium and includes a plurality of instructions to allow a computer device (which can be a personal computer, a server, or network equipment, etc.) to perform all or part of the steps of the method described in each embodiment of the present invention. The aforementioned storage medium includes a USB flash drive, a mobile hard disk drive, a read-only memory (ROM), a random access memory (RAM), a magnetic disk, an optical disc, and other media that can store program codes.

An embodiment of the present invention discloses a computer program product. The computer program product includes a computer program stored on a non-transient computer-readable storage medium, and the computer program includes program instructions. When the program instructions are executed by a computer, the computer is configured to execute the method provided by the above methods of the embodiments, for example, including: obtaining a cell volume and a critical value of a centrifugal device after centrifugal stabilization of the centrifugal device; and performing, according to a magnitude relationship between the cell volume and the critical value of the centrifugal device, a velocity reduction process on a centrifugal chamber by combining the cell volume and the centrifugal chamber information.

An embodiment of the present invention provides a non-transient computer-readable storage medium, and the non-transient computer-readable storage medium stores server instructions. The computer instructions allow a computer to execute the method provided by the above methods of the embodiments, for example, including: obtaining a cell volume and a critical value of a centrifugal device after centrifugal stabilization of the centrifugal device: and performing, according to a magnitude relationship between the cell volume and the critical value of the centrifugal device, a velocity reduction process on a centrifugal chamber by combining the cell volume and the centrifugal chamber information.

The devices of the embodiments described above are only exemplary. Specifically, the unit described as a separate unit may or may not be physically separate, and the component as a display unit may or may not be a physical unit, that is, the component can be located in one place, or can be distributed over a plurality of network elements. Some or all of the modules can be selected according to the actual needs to achieve the objective of the embodiment solution, which can be understood and implemented by those skilled in the art without creative work.

Through the description of the above embodiments, those skilled in the art can clearly understand that each embodiment can be realized using software and a necessary general hardware platform, or can be realized through hardware. Based on this understanding, the above technical solution, in essence, is that the part that contributes to the prior art can be reflected in the form of a software product. The computer software product can be stored in a computer-readable storage medium, such as a ROM/RAM, a magnetic disk, an optical disc, and the like, and includes a plurality of instructions to allow a computer device (which can be a personal computer, a server, or network equipment, etc.) to perform the method described in each embodiment or a part of the embodiment.

Finally, it should be noted that the above embodiments are only used to illustrate the technical solutions of the present invention, rather than to limit the technical solutions of the present invention. Although the present invention is described in detail with reference to the above embodiments, those having ordinary skill in the art should understand that they can still modify the technical solutions recorded in the above embodiments or equally replace some of the technical features therein, while these modifications or replacements do not cause the essence of the corresponding technical solutions to deviate from the spirit and scope of the technical solutions of the embodiments of the present invention.

What is claimed is:

1. A method for automatic cell centrifugal cleaning and medium replacement, comprising:
obtaining a cell volume and a critical value of a centrifugal device after centrifugal stabilization of the centrifugal device; and performing, according to a magnitude relationship between the cell volume and the critical value of the centrifugal device, a velocity reduction process on a centrifugal chamber by combining the cell volume and centrifugal chamber information;
wherein the centrifugal chamber information comprises chamber length information, chamber height information, and chamber radius information, wherein
the chamber length information is a distance from an outer wall of the centrifugal chamber to an outlet position of the centrifugal device;
the chamber height information is a height of the centrifugal chamber; and
the chamber radius information is a radius of the centrifugal chamber.

2. The method according to claim 1, wherein the step of performing, according to the magnitude relationship between the cell volume and the critical value of the centrifugal device, the velocity reduction process on the centrifugal chamber by combining the cell volume and the centrifugal chamber information comprises:
when the cell volume is less than the critical value of the centrifugal device, calculating a rotation velocity for a velocity reduction of the centrifugal chamber according to the cell volume, the chamber length information, and the chamber radius information, and performing the velocity reduction process on the centrifugal chamber according to the rotation velocity for the velocity reduction of the centrifugal chamber.

3. The method according to claim 1, wherein the step of performing, according to the magnitude relationship between the cell volume and the critical value of the centrifugal device, the velocity reduction process on the centrifugal chamber by combining the cell volume and the centrifugal chamber information comprises:
when the cell volume is equal to the critical value of the centrifugal device, calculating a rotation velocity for a velocity reduction of the centrifugal chamber according to the chamber length information and the chamber radius information, and performing the velocity reduction process on the centrifugal chamber according to the rotation velocity for the velocity reduction of the centrifugal chamber.

4. The method according to claim 1, wherein the step of performing, according to the magnitude relationship between the cell volume and the critical value of the centrifugal device, the velocity reduction process on the centrifugal chamber by combining the cell volume and the centrifugal chamber information comprises:
when the cell volume is larger than the critical value of the centrifugal device, calculating a rotation velocity for a velocity reduction of the centrifugal chamber according to the cell volume, the chamber length information, the chamber radius information, and the height of the centrifugal chamber, and performing the velocity reduction process on the centrifugal chamber according to the rotation velocity for the velocity reduction of the centrifugal chamber.

5. An electronic device, comprising a memory, a processor, and a computer program, wherein the computer program is stored on the memory and configured to run on the processor, wherein when the computer program is executed by the processor, steps of the method according to claim 1 are implemented.

6. The electronic device according to claim 5, wherein in the method, the step of performing, according to the magnitude relationship between the cell volume and the critical value of the centrifugal device, the velocity reduction process on the centrifugal chamber by combining the cell volume and the centrifugal chamber information comprises:

when the cell volume is less than the critical value of the centrifugal device, calculating a rotation velocity for a velocity reduction of the centrifugal chamber according to the cell volume, the chamber length information, and the chamber radius information, and performing the velocity reduction process on the centrifugal chamber according to the rotation velocity for the velocity reduction of the centrifugal chamber.

7. The electronic device according to claim 5, wherein in the method, the step of performing, according to the magnitude relationship between the cell volume and the critical value of the centrifugal device, the velocity reduction process on the centrifugal chamber by combining the cell volume and the centrifugal chamber information comprises:

when the cell volume is equal to the critical value of the centrifugal device, calculating a rotation velocity for a velocity reduction of the centrifugal chamber according to the chamber length information and the chamber radius information, and performing the velocity reduction process on the centrifugal chamber according to the rotation velocity for the velocity reduction of the centrifugal chamber.

8. The electronic device according to claim 5, wherein in the method, the step of performing, according to the magnitude relationship between the cell volume and the critical value of the centrifugal device, the velocity reduction process on the centrifugal chamber by combining the cell volume and the centrifugal chamber information comprises:

when the cell volume is larger than the critical value of the centrifugal device, calculating a rotation velocity for a velocity reduction of the centrifugal chamber according to the cell volume, the chamber length information, the chamber radius information, and the height of the centrifugal chamber, and performing the velocity reduction process on the centrifugal chamber according to the rotation velocity for the velocity reduction of the centrifugal chamber.

9. A non-transient computer-readable storage medium, storing a computer program, wherein when the computer program is executed by a processor, steps of the method according to claim 1 are implemented.

10. The non-transient computer-readable storage medium according to claim 9, wherein in the method, the step of performing, according to the magnitude relationship between the cell volume and the critical value of the centrifugal device, the velocity reduction process on the centrifugal chamber by combining the cell volume and the centrifugal chamber information comprises:

when the cell volume is less than the critical value of the centrifugal device, calculating a rotation velocity for a velocity reduction of the centrifugal chamber according to the cell volume, the chamber length information, and the chamber radius information, and performing the velocity reduction process on the centrifugal chamber according to the rotation velocity for the velocity reduction of the centrifugal chamber.

11. The non-transient computer-readable storage medium according to claim 9, wherein in the method, the step of performing, according to the magnitude relationship between the cell volume and the critical value of the centrifugal device, the velocity reduction process on the centrifugal chamber by combining the cell volume and the centrifugal chamber information comprises:

when the cell volume is equal to the critical value of the centrifugal device, calculating a rotation velocity for a velocity reduction of the centrifugal chamber according to the chamber length information and the chamber radius information, and performing the velocity reduction process on the centrifugal chamber according to the rotation velocity for the velocity reduction of the centrifugal chamber.

12. The non-transient computer-readable storage medium according to claim 9, wherein in the method, the step of performing, according to the magnitude relationship between the cell volume and the critical value of the centrifugal device, the velocity reduction process on the centrifugal chamber by combining the cell volume and the centrifugal chamber information comprises:

when the cell volume is larger than the critical value of the centrifugal device, calculating a rotation velocity for a velocity reduction of the centrifugal chamber according to the cell volume, the chamber length information, the chamber radius information, and the height of the centrifugal chamber, and performing the velocity reduction process on the centrifugal chamber according to the rotation velocity for the velocity reduction of the centrifugal chamber.

13. A device for automatic cell centrifugal cleaning and medium replacement, comprising:

an acquisition module configured to obtain a cell volume and a critical value of a centrifugal device after centrifugal stabilization of the centrifugal device; and a velocity reduction and medium replacement module configured to perform, according to a magnitude relationship between the cell volume and the critical value of the centrifugal device, a velocity reduction process on a centrifugal chamber by combining the cell volume and centrifugal chamber information;

wherein the centrifugal chamber information comprises chamber length information, chamber height information, and chamber radius information, wherein the chamber length information is a distance from an outer wall of the centrifugal chamber to an outlet position of the centrifugal device;

the chamber height information is a height of the centrifugal chamber; and the chamber radius information is a radius of the centrifugal chamber.

* * * * *